US005662904A

United States Patent [19]

Ferguson et al.

[11] Patent Number: 5,662,904
[45] Date of Patent: Sep. 2, 1997

[54] ANTI-SCARRING COMPOSITIONS COMPRISING GROWTH FACTOR NEUTRALIZING ANTIBODIES

[75] Inventors: Mark William James Ferguson, Stockport, England; David Michael Foreman, Chorlton; Mamta Shah, Withington, both of United Kingdom

[73] Assignee: The Victoria University of Manchester, Manchester, England

[21] Appl. No.: 122,508

[22] PCT Filed: Mar. 30, 1992

[86] PCT No.: PCT/GB92/00570

§ 371 Date: Sep. 27, 1993

§ 102(e) Date: Sep. 27, 1993

[87] PCT Pub. No.: WO92/17206

PCT Pub. Date: Oct. 15, 1992

[30] Foreign Application Priority Data

Mar. 28, 1991 [GB] United Kingdom .............. 9106678

[51] Int. Cl.[6] .............. A61K 39/395; A61K 39/44; C07K 16/22; C07K 17/04
[52] U.S. Cl. .............. 424/130.1; 424/145.1; 530/387.1; 530/388.24; 530/391.1; 530/391.7
[58] Field of Search .............. 530/387.1, 388.23, 530/388.22, 389.2, 412; 435/240.27, 70.21; 424/130.1, 143.1, 145.1, 158.1

[56] References Cited

U.S. PATENT DOCUMENTS

| 4,837,381 | 6/1989 | Steber et al. .............. 424/502 |
| 4,886,747 | 12/1989 | Derynck et al. .............. 435/69.4 |
| 4,931,548 | 6/1990 | Lucas et al. .............. 530/399 |
| 5,055,447 | 10/1991 | Palladino et al. .............. 514/12 |
| 5,104,977 | 4/1992 | Sporn et al. .............. 530/399 |
| 5,168,051 | 12/1992 | Derynck et al. .............. 435/69.4 |
| 5,520,926 | 5/1996 | Ferguson . |

FOREIGN PATENT DOCUMENTS

| 0 105 014 | 4/1984 | European Pat. Off. .......... A61K 37/02 |
| 0 128 849 | 12/1984 | European Pat. Off. .......... C07G 7/00 |
| 0 159 276 | 10/1985 | European Pat. Off. .......... A61K 37/02 |
| 0 169 016 | 1/1986 | European Pat. Off. .......... C07K 13/00 |
| 0 200 090 | 12/1986 | European Pat. Off. .......... A61K 37/02 |
| 0 200 341 | 12/1986 | European Pat. Off. .......... C12N 15/00 |
| 0 282 317 | 9/1988 | European Pat. Off. .......... C07K 13/00 |
| 0 375 127 | 6/1990 | European Pat. Off. .......... A61K 37/02 |
| 0 433 225 | 6/1991 | European Pat. Off. .......... C07K 7/00 |
| 0 526 756 | 2/1993 | European Pat. Off. .......... A61K 37/36 |
| 0 542 679 | 5/1993 | European Pat. Off. .......... C12N 15/12 |
| 88/05788 | 8/1988 | WIPO .............. C07K 15/00 |
| 89/12101 | 12/1989 | WIPO .............. C12N 15/00 |
| 90/00903 | 2/1990 | WIPO .............. A61K 45/06 |
| 90/03810 | 4/1990 | WIPO .............. A61G 15/46 |
| 90/03812 | 4/1990 | WIPO .............. A61L 27/00 |
| WO91/04748 | 4/1991 | WIPO . |
| 91/04748 | 4/1991 | WIPO .............. A61K 39/395 |
| 91/10727 | 7/1991 | WIPO .............. C12N 5/00 |
| 92/00318 | 1/1992 | WIPO .............. C07K 3/20 |
| 92/00330 | 1/1992 | WIPO .............. C07K 15/28 |
| 92/13073 | 8/1992 | WIPO .............. C12N 15/12 |
| 92/13551 | 8/1992 | WIPO .............. A61K 37/02 |
| WO93/19769 | 10/1993 | WIPO . |
| WO95/26203 | 10/1995 | WIPO . |

OTHER PUBLICATIONS

Shah, Mamta et al., *Control Of Scarring In Adult Wounds By Neutralising Antibody To Transforming Growth Factor*, The Lancet, vol. 339, Jan. 25, 1992, pp. 213–214.

Kovacs, Elizabeth J., *Fibrogenic Cytokines: The Role Of Immune Mediators In The Development Of Scar Tissue*, Immunology Today, vol. 12, No. 1, 1991, pp. 17–23.

Roberts, A.B. et al., *The Transforming Growth Factor βs*, Peptide Growth Factors And Their Receptors, (1990) Springer–Verlag, Berlin, pp. 418–472.

Amento, Edward P. et al., *TGF–β And Wound Healing*, (1991, Clinical Applications of TGF–β, Wiley, Chicester, (Ciba Foundation Symposium, 157), pp. 115–129.

Logan, Ann, et al., *Effects Of Transforming Growth Factor β1 On Scar Production In The Injured Central Nervous System Of The Rat*, European Journal Of Neuroscience, 1994, vol. 6, pp. 355–363.

Shah, M., et al., *Modulation Of PDGF And Basic FGF In Incisional Cutaneous Wounds Reduces Scarring In Adult Rodents*, 4th Annual Meeting of the European Tissue Repair Society, 1994, p. 293.

Yu Yamaguchi et al., *Negative Regulation of Transforming Growth Factor–β by the Proteoglycan Decorin*, Letters to Nature, vol. 346, pp. 281–284 (1990).

Bryan Sykes et al., *The Estimation of Two Collagens From Human Dermis by Interrupted Gel Electrophoresis*, Biochemical and Biophysical Research Communications, vol. 72, No. 4, pp. 1472–1480 (1976).

Hermann Stegemann et al., *Determination of Hydroxyproline*, Clinica Chimica ACTA, vol. 18, pp. 267–273 (1967).

Thomas A. Mustoe et al., *Accelerated Healing of Incisional Wounds in Rats Induced by Transforming Growth Factor–β*, Science Reports, vol. 237, pp. 1333–1336 (1987).

Harlow & Lane "Antibodies A Laboratory Manual" CSHL Press 1988 pp. 285, 287.

Michael B. Sporn et al., *Polypeptide Transforming Growth Factors Isolated from Bovine Sources and Used for Wound Healing in vivo*, Science, vol. 219, pp. 1329–1331 (1983).

Gregory L. Brown et al., *Enhancement of Epidermal Regeneration by Biosynthetic Epidermal Growth Factor*, J. Exp. Med., vol. 163, pp. 1319–1324 (1986).

(List continued on next page.)

Primary Examiner—Toni R. Scheiner
Assistant Examiner—Nancy A. Johnson
Attorney, Agent, or Firm—Wallenstein & Wagner, Ltd.

[57] ABSTRACT

A composition for use in the treatment of wounds to inhibit scar tissue formation during healing, comprising an effective amount of an activity-inhibiting growth factor neutralizing agent or agents specific against all TGF-β, except for TGF-β$_3$, and PDGF, together with a pharmaceutically acceptable carrier. A method of preparing the composition and a method of administering the composition to a host suffering from tissue wounding is also disclosed.

28 Claims, No Drawings

OTHER PUBLICATIONS

George A. Ksander, *Exogenous Growth Factors in Dermal Wound Healing*, Annual Reports in Medicinal Chemistry, vol. 24, pp. 223–232 (1989).

Mary H. McGrath, *Peptide Growth Factors and Wound Healing*, Clinics in Plastic Surgery, vol. 17, No. 3, pp. 421–432 (Jul. 1990).

Renzo Cappelletti et al., *A New Electrophoretic Method for the Complete Separation of all Known Animal Glycosaminoglycans in a Monodimensional Run*, Analytical Biochemistry, vol. 99, pp. 311–315 (1979).

Fingl et al (1975), In (Goodman et al, eds.) "The Pharmacological Bases of Therapeutics", MacMillan–Publishing Co., Inc., pp. 1–46.

Gregoriades et al (1993) Trends in Biotech. 11:440–442.

Roitt (1991) "Essential Immunology", Blackwell Scientific Publications, Oxford, pp. 65–68 & 74.

ANTI-SCARRING COMPOSITIONS COMPRISING GROWTH FACTOR NEUTRALIZING ANTIBODIES

This invention relates to the healing of wounds and no agents and techniques for facilitating repair and healing of animal tissue, especially, but not exclusively, skin or other epithelial tissue, that has been damaged by, for example, wounds resulting from accidental injury, surgical operations or other trauma. The invention has particular reference to the healing of wounds in humans and other vertebrates.

As is well known, the healing of wounds in tissue such as skin generally involves, at least in adult humans and other mammals, a process of extra-cellular matrix (ECM) biosynthesis, turnover and organisation which commonly leads to the production of fibrous, connective tissue scars and consequential loss of normal tissue function.

In the realm of surgery scar tissue formation and contraction is a major clinical problem for which there is no entirely satisfactory solution at present. Likewise, scarring and fibrosis following accidental burning or other injuries or trauma, particularly in children, often has serious results, leading to impaired function, defective future growth, and to unsightly aesthetic effects, and again presents a major problem.

In regard to unsightly aesthetic effects produced by scars, there also commonly arises a need for cosmetic treatment or operations to attempt to remove these disfigurements in order to improve appearance. Additionally, a similar need for cosmetic treatment often arises in connection with unwanted tatoos and other skin blemishes. At present, however, it is difficult or impossible to carry out such cosmetic treatment or operations satisfactorily since a certain amount of surgery is generally involved which in itself is likely to result in wounds producing fresh unsightly scar tissue.

In adult humans and other mammalian vertebrates, wound healing in tissues such as skin is generally a reparative process, in contrast to a regenerative process which appears to take place in healing of fetal and embryonic tissue. The outcome of a wound repair process appears no be influenced by a number of different factors, including both intrinsic parameters, e.g. tissue oxygenation; and extrinsic parameters, e.g. wound dressings. There is, however, considerable evidence indicating that the overall process of healing and repair of wound damaged tissue, including the necessary innercellular communication, is regulated in a coordinated manner in adult humans and other mammals by a number of specific soluble growth factors which are released within the wound environment (especially by degranulating platelets and incoming macrophages) and which, amongst other things, appear to induce neovascularisation, leucocyte chemotaxis, fibroblast proliferation, migration and deposition of collagen and other extracellular matrix molecules within the wounds. Such growth factors that have been identified and isolated are generally specialised soluble proteins or polypeptides and include transforming growth factor alpha (TGF-$\alpha$), transforming growth factor beta (TGF-$\beta$1, TGF-$\beta$2, TGF-$\beta$3 etc), platelet derived growth factor (PDGF), epidermal growth factor (EGF), insulin-like growth factors I and II (IGFI and IGFII) and acidic and basic fibroblast growth factors (acidic FGF and basic FGF). Many of these growth factors have already been made by genetic engineering using recombinant DNA technology.

General reviews of these growth factors are to be found in articles by Mary H McGrath in *Clinics in Plastic Surgery*, Vol. 17, No. 3, July 1990, pp 421–432, and by George A Ksander in *Annual Reports in Medicinal Chemistry*, 1989, Vol. 24, pages 223–32 (published by Academic Press, Inc.) of which the contents are incorporated herein by reference.

The recognition of the importance of the role of such growth factors in the control of wound healing has led to numerous proposals for their clinical use and application as exogenous growth factor agents in treatment for acceleration and promotion of healing of wounds, especially in cases of defective wound healing states (see for example Sporn et al, *Science* (1983) 219, 1329–1331; Brown et al, *J. Exp. Med.* (1986) 153, 1319–1324; Mustoe et al, *Science* (1987) 237, 1333–1336), and this has been the main trend in endeavouring to develop therapeutic applications of the knowledge acquired about these growth factors.

According to the present invention there is provided a composition for use in the treatment of wounds to inhibit scar tissue formation during healing, comprising an effective activity-inhibiting amount of a growth factor neutralising agent or agents specific against only fibrotic growth factors together with a pharmaceutically acceptable carrier.

The TGF-$\beta$ growth factor family, for example, is believed to have a particularly important regulating role in wound repair, especially in adult animals, as a stimulant of macrophage infiltration, fibroblast migration, and extracellular matrix synthesis, especially collagen synthesis and deposition by fibroblasts which are involved in the production of scar tissue. Other growth factors, e.g. PDGF, are also important in this process and, to some extent, are believed to act in cooperation with one another in the complex overall regulatory process that is involved in wound healing. Indeed, PCT/US90/05566 discloses the general use of antibodies to TGF-$\beta$ to reduce fibrosis in a rat kidney nephrosis induced model. However, it is now found that not all TGF-$\beta$ growth factors are fibrotic and that supressing the activity of TGF$\beta$-3 in particular is counter-productive.

PCT/US90/05566 mentions TGF$\beta$-1 and TGF$\beta$-2 as having the function of increasing extracellular matrix production, but does not suggest that any particular TGF$\beta$ does not have such an effect.

The growth factor neutralising agent may be a growth factor neutralising antibody, for example antibodies to TGF-$\beta$1, TGF-$\beta$2 and PDGF.

The growth factor neutralising agent may be a growth factor receptor blocking agent, for example a peptide containing the receptor binding site of the growth factors TGF-$\beta$1, TGF-$\beta$2.or PDGF, for example.

The growth factor neutralising agent may also comprise a molecule which binds to the growth factor to inhibit receptor binding, for example where the growth factor is selected from TGF-$\beta$1 and TGF-$\beta$2, the molecule may be selected from Decorin and Biglycan.

The growth factor neutralising agent may also be an antisense oligonucleotide or ribosyme(s) to growth factor mRNA, which both act to prevent mRNA from being translated.

The growth factor neutralising agent may also be a soluble form of the receptor or the growth factor binding domain of the receptor.

The growth factor neutralising agent may be present in the composition in an active form. Alternatively, the growth factor neutralising agent may be present in an inactive form.

One method of inactivating the growth factor neutralising agent is encapsulation, whereby the capsules may be degradable by an external stimulus to release the active growth factor neutralising agent when required.

The external stimulus may include UV light, in vivo enzymes, ultrasound or heat.

A second method of inactivating the growth factor neutralising agent may be by the molecular addition of a binding molecule.

Again, the binding molecule may be detached from the complex to release active growth factor neutralising agent by an external stimulus including UV light, in vivo enzymes, ultrasound or heat.

The pharmaceutically acceptable carrier may comprise a neutral sterile cream, gel or powder for topical application, or a sterile solution for injection, irrigation or inhalation or an aerosol, or may comprise a sterile dressing for topically covering a wound or may be in the form of a tablet or capsule for endoral administration, or the carrier may comprise a biopolymer patch or a slow release device for implantation.

The composition may also comprise active cytokines, for example fibroblast growth factor or factors or other cell proliferation or migration stimulating or glyco-aminoglycan stimulating factors in a ratio sufficient to accelerate wound healing in addition to the growth factor neutralising agent(s) reducing wound scarring.

The invention also provides a method of preparation of a pharmaceutical composition containing the growth factor neutralising agent or agents for applying the composition topically in a cream, gel, powder or dressing; in a solution for injection, irrigation or inhalation or aerosol, or in the form of a tablet or capsule for enteral administration. The pharmaceutical preparation may also comprise a biodegradable polymer forming a patch, or an implantable control release device, useful in surgical operations having a large initial release followed by a slower release later. It will be appreciated that this list is not exhaustive, many other types of compositions being possible, such as might readily occur to one skilled in the art.

The method of preparation of the composition may also include a composition comprising active cytokines.

The invention also provides a method of inhibiting scar tissue formation during the healing of wounds, said method consisting in adminstering to a host suffering from tissue wounding a growth factor neutralising agent or agents in the wound area in a dosage effective to reduce activity of one or more growth factors involved in the process that leads to the formation of scar tissue during healing.

Preferably, the inhibitory agent or mixture of agents employed for this purpose comprises a neutralising antibody or antibodies specific to one or more of the growth factors concerned, or to precursors of such growth factors advantageously, such antibody or each such antibody, is a monoclonal antibody obtained by recombinant DNA techniques. However, polyclonal antibodies, purified for example by affinity chromotography from antiserum prepared by injection of relevant growth factor(s) in an appropriate host, may also be used quite satisfactorily as an alternative, as has been the case in most of the preliminary experimental investigations. If desired, instead of complete antibodies, fragments thereof (Fab's) retaining the specific antigen binding characteristics can also be used and such fragments are intended to be included within the scope of the term "antibody" as used herein in this specification.

In regard to precursors of these growth factors, it is known that in many cases the growth factors are initially present in an inactive state as part of, or as a ligand bound to, a larger protein molecule, and are separated from the latter, e.g. by enzymic action, when released in their active form. Binding of a neutralising agent such as an antibody to such inactive protein precursors may therefore prevent or inhibit proteolytic action and release of the active growth factors which will lead to an overall neutralising effect and inhibition of activity in the same way as the alternative process of a direct binding of an inhibitory agent to the active growth factor molecules themselves or to cellular receptor sites of such growth factors.

Instead of using growth factor neutralising antibodies, the inhibitory agent or mixture of agents may alternatively consist of a synthetic peptide or peptides that can act to antagonise or block growth factor activity, e.g. by blocking binding of the growth factor(s) at cellular receptor sites without eliciting any intracellular "second messenger" response. Such peptide "blocking" agents could have the advantage of being free of potential adverse immunogenic effects, and may pass through membrane barriers more easily than antibodies so that they would be most suitable for making up pharmaceutical formulations or compositions for topical application. These "blocking" peptides may readily be designed from knowledge of the amine acid sequence of the growth factors concerned and of that portion of this sequence which is involved in binding to the cellular receptors since these peptides will need to "mimic" this binding portion of the sequence. It is, for instance, known that with TGF-$\beta$1 it is the c-terminal region of the molecule that is involved in receptor binding. Similarly, the region(s) involved in receptor binding with TGF-$\alpha$ is the region between cys 33 and cys 42, and with EGF it is the regions between cys 20 and cys 31, between tyrosine 14 and cys 31 and between leucine 15 and arginine 53 that are involved. With FGF's the critical receptor binding region is that between amine acids 105 and 115.

As a further possibility, the inhibitory growth factor neutralising agent(s) may consist of other molecular entities that act by binding directly to a growth factor or factors, or precursor(s) thereof, to inactivate the latter. An example of a neutralising or inhibitory agent of this kind is Decorin which is a small chrondroitin-dermatan sulphate proteoglycan known to strongly bind TGF-$\beta$, as reported by Yamaguchi et al, *Nature* (1990), 346, 281-284.

Alternatively, the inhibitory growth factor neutralising agent(s) may be active at the molecular level and consist of molecules active against a growth factor's mRNA. Such molecules may include antisense oligonucleotide(s) synthesised against one or more growth factor mRNA sequences to prevent translation thereof, or the molecule may be a ribosyme(s) targetted against specific sequences of one or more growth factor mRNA sequences to destroy the mRNA and again prevent its translation.

Although use of an antibody or other agent having a neutralising effect in respect of only one growth factor that is involved in the formation of scar tissue during wound healing, especially TGF-$\beta$1 and 2 or PDGF for example, may be quite sufficient to prevent and significant amount of scar tissue from being produced In some cases combined adminstration of two or more different antibodies or other inhibitory agents having a neutralising effect against two or more different growth factors concerned may be found to be even more effective, especially for relatively large excisional wounds for example. In this case, the different or other inhibitory agents may be administered separately but simultaneously or sequentially, or they may be made up into a mixture or "cocktail" within a single pharmaceutical formulation.

Although it is believed that a series of these growth factors, including at least those of the TGF-$\beta$ family and PDGF, normally act in cooperation with one another in an orchestrated manner to regulate the overall process of wound healing, including the steps leading to the production of scar tissue, the effect on production of scar tissue of reducing or neutralising activity of any one growth factor is likely to vary depending on the nature or identity of that growth factor and on the form of the resultant active growth factor profile. Thus, whilst inhibition of the activity of TGF-β and/or PDGF can generally be very effective in this respect, inhibition of the activity of certain of the other growth factors may, at least on its own, be less effective under similar conditions for reducing scar tissue formation, even though such other growth factors may still be necessary, or may at least have a beneficial effect, in connection with promoting wound healing.

There can therefore be a further possibility in applying the invention of using an inhibitory or neutralising agent or agents effective in reducing activity of a growth factor or factors e.g. TGF-β and/or PDGF, having a major role in the formation of scar tissue in combination with a different exogeneous growth factor or agent which does non independently promote the formation of scar tissue to any significant extent but which, at the same time, can independently promote wound healing or provide a beneficial effect in respect of quality of healing. At least in some cases, such other additional exogeneous growth factor, for use in combination with TGF-β or PDGF neutralising agent(s) for example, may be provided by fibroblast growth factors (FGF's). Thus, by providing a pharmaceutical preparation having a ratio of the active cyctokine FGF to TGF-β and/or PDGF neutralising agent(s), a preparation may be obtained which not only prevents scarring of a wound, but also accelerates the whole process of wound healing.

It might have been anticipated that any treatment for reducing or preventing scar tissue formation would be most effectively applied at a relatively late stage of healing during the phase of tissue remodelling or reorganisation that occurs subsequent to the formation of granulation tissue which replaces fibrin initially produced in the early stages of healing. Contrary to such expectation, however it has been found, surprisingly, that in applying the present invention the treatment with the growth factor neutralising agent or agents may need to be carried out at an early stage of healing in order to be effective. In general, the treatment is best carried out before and/or during the granulation phase whilst fibrin is still present, i.e. before the fibrin has been wholly replaced by granulation tissue. This will usually be within a period of about 14 days after the initial occurrence of a wound. Preferably, however, treatment will be commenced earlier, within seven days or, if possible, within three days or less following wounding. Indeed, it may often be most advantageous to commence treatment on the same day as wounding, or at least on the following day, and in the case of surgical wounds the commencement of this treatment, say by topical or parenteral application of the growth factor neutralising agent(s) in a pharmaceutical formulation applied to the wound area, may well be incorporated as an integral part of the surgical procedure and be applied before surgery or immediately the main surgery is completed, before or after suturing.

It has also been found, again somewhat surprisingly, that the treatment does not necessarily need to be repetitive and to be continued throughout all the phases of wound healing. In order to be effective, it may often be sufficient to administer the growth factor neutralising agent(s) in an appropriate dosage once, or only a few times at most, during the early stages of wound healing. This is of course important where agents such as proteins are concerned which may tend to provoke immunological reactions, and it also gives other practical and economic advantages.

Although it is possible that in some cases the overall time to achieve complete healing of a wound may be somewhat extended upon applying this treatment, any increase in overall healing time may well be more than adequately compensated for by the improved quality of the healed wound. A noteworthy and further surprising feature of the experimental work so far conducted, however, is that no really significant increase in overall healing time has been observed, nor has there been any impairment of wound strength upon healing. Indeed, in respect of this latter point, it would seem that wound strength may even be improved in that the orientation observed of the new collagen fibres or fibrils formed during healing, at least in the case of incisional dermal wounds, more closely resembled that of undamaged tissue, lying generally parallel to the outer skin surface instead of at a large angle or generally perpendicular to the outer surface as is commonly found when such wounds heal normally with formation of scar tissue.

By way of further background explanation and description of the invention, illustrative examples are hereinafter presented of some of the investigations made and results obtained in the development of the invention, from which the skilled person in the art will more readily be able to appreciate the nature thereof and to put the invention into practical effect.

First there follows an outline or summary of the materials, methods and techniques which have generally been used, unless subsequently stated otherwise, in the investigations and illustrative examples referred to.

The preliminary experimental work in these investigations was carried out using rats as model experimental animals, but the results are applicable generally to humans and other animals.

Adult, male, Sprague-Dawley rats weighing between 200–250 grammes were anaesthetised with halothane/nitrous oxide/oxygen inhalation. After locally clipping the fur, four linear full-thickness incisions, 10 mm in length, were made on the dorsal skin of the animal, equidistant from the midline and adjacent to its four limbs.

In each animal one wound (control) was unmanipulated, one (sham control) was injected with an irrelevant antibody, one (the positive control) was injected with a growth factor detailed below, and one (the experimental wound) was injected with a preparation of appropriate growth factor neutralising antibody or antibodies. The experiments were conducted on groups of these animals, and according to which group was concerned the injections (100 μl each) were carried out daily for either a period of three consecutive days or seven consecutive days, starting either on the day of wounding, or on the following day, or in a few groups at a much later stage, e.g. 7 days or 19 days post-wounding.

In each group, at least two animals were usually killed (by chloroform overdose on post-wounding days 7, 14, 29 and 42, and in some cases also on post-wounding days 70, 112 and 168. All four wounds were excised with a 0.5 cm margin on all sides immediately after death of each animal and were subjected to tissue analysis by conventional immunohistochemical, histological staining and biochemical techniques.

Generally, for carrying out this analysis, each wound was bisected to-provide two samples which were either frozen and/or fixed and processed for immunocytochemical staining using antibodies to collagens I, III, IV, laminin and fibronectin or processed for routine histological examination using a variety, of connective tissue stains, or they were immediately freeze-dried for biochemical analyses after microscopic dissection.

In the immunohistochemical analyses, primary and secondary antibodies for indirect immunostaining were used as shown in the following tables.

TABLE 1

Primary Antibodies

| Raised Against | Host | Source | Dilution | Secondary Ab (Table 2 ref) |
|---|---|---|---|---|
| HUMAN FIBRONECTIN | SHEEP | a | 1:100 | 1 |
| MOUSE LAMININ | RABBIT | b | 1:50 | 2 |
| RAT TYPE I COLLAGEN | RABBIT | b | 1:50 | 2 |
| RAT TYPE III COLLAGEN | RABBIT | b | 1:50 | 2 |
| RAT TYPE IV COLLAGEN | RABBIT | b | 1:100 | 2 |
| RAT MACROPHAGES | MOUSE | a | 1:200 | 3 & 4 |
| RAT MONOCYTES & MACROPHAGES | MOUSE | a | 1:200 | 3 & 4 |
| HUMAN FACTOR VIII | RABBIT | c | 1:200 | 2 |

TABLE 2

Secondary Antibodies

| Raised Against | Host | Source | Dilution | (Table 1 ref) |
|---|---|---|---|---|
| SHEEP IgG | DONKEY | a | 1:40 | 1 |
| RABBIT IgG | SWINE | c | 1:40 | 2 |
| MOUSE IgG | SHEEP | d | 1:200 | 3 |
| STREPTAVIDINE |  | d | 1:100 | 4 |

Key to Source Codes

| | |
|---|---|
| a | SEROTEC LTD, Oxford, UK. |
| b | Institut Pasteur de Lyon, France. |
| c | DAKOPATTS, Copenhagen, Denmark. |
| d | AMERSHAM, INTERNATIONAL Plc, Amersham, UK. |

Note:
Secondary antibodies 1, 2 and 4 were FITC conjugated (fluorescein isothiocyanate labelled) for immunofluorometric detection and measurement; 3 was biotynlated.

In carrying out the indirect immunostaining, the incubation with the primary antibody was for 1 hour followed by three rinses in phosphate buffered saline (PBS). Incubation with FITC-conjugated secondary antisera was for 1-hour followed by a further three rinse with PBS. Immunostaining for macrophages and monocytes involved the Biotin-Streptavidine technique, i.e. after the primary incubation and rinsing, the sections were incubated with the biotynlated sheep antimouse IgG for 1 hour, rinsed with PBS three times, incubated with the fluorescein streptavidine for 20 minutes and finally washed with PBS three times. The sections were mounted in a non-fading medium, DABCO (1,4-diazobicyclo-(2,2,2)-octane), and photographed using a Leitz Dialux microscope and kodak Ektachrome 400 ASA film.

For each primary antibody and each wound control sections were stained, substituting PBS for the primary antibody.

In carrying out the routine histology staining, cellularity of the wounds was studied by staining cryosections of the tissue (post-fixed in Bouins fluid) with Harris's haematoxylin and eosin, and collagen deposition in the wounds was studied by staining cryosections with Masson's trichrome and Hughesdon's modification of Mallory's trichrome stains.

For the biochemical analyses, the wounds were microscopically dissected out along with a piece of unwounded dorsal skin from each wound and immediately freeze-dried to constant weight. The tissue was homogenised in 1 ml of 1M guanidine hydrochloride, 0.15M sodium acetane, 0.01M EDTA, pH 5.8, for 24 hours at 4° C. to extract the glycosaminoglycans. The homogenate was then centrifuged at 18,000 g for 1 hour. The pellet was washed twice with 0.5 ml of water and the washings added to the supernatant. The supernatant was dialysed against 100 mM phosphate buffer-with 5 mM EDTA, pH 6.5, followed by digestion with papain 2.5 mg/ml. The glycosaminoglycans were precipitated with 2% CPC and separated using the method of Cappelletti et al, 1979.

After washing, the pellets were digested with pepsin 100 82 g/ml in 0.5M acetic acid at 4° C. for 24 hours. This was followed by centrifuging at 18,000 g for 1 hour. The pellet thus obtained was subjected Hydroxyproline assay as described by Stegman and Stadler (1967); some of the supernatant was also used for this assay. To measure the ratio of type I/III collagen, the supernatant was subjected to SDS PAGE using the method of Sykes et al (1976).

The growth factors used in these experiments were commercially available reagents obtained from R & D Systems (Mineapolis, U.S.A.) or British Biotechnology (U.K.) or Serotec (U.K.) and included:

1. Transforming growth factor beta-1 (TGF-$\beta$1) derived from porcine platelets—Dose 10 ng/injection,
2. Platelet derived growth factor (PDGF) from porcine platelets—Dose 10 ng/injection.
3. Epidermal growth factor (EGF) derived from mouse salivary gland—Dose 10 ng/injection.
4. Basic Fibroblast growth factor (bFGF) derived from bovine brain—Dose 10 ng/injection.
5. Acidic Fibroblast growth factor (aFGF) derived from bovine brain—Dose 10 ng/injection.

The growth factor neutralising antibodies used in these experiments were also reagents commercially available as detailed above and were of known neutralising potency. They included:

1. TGF Beta neutralising antibody (raised in rabbit against native porcine platelet TGF-$\beta$1—neutralises both TGF$\beta$-1 and TGF$\beta$-2)—Dose 50 µg/injection.
2. PDGF neutralising antibody (raised in goats against native human PDGF)—Dose 20 µg/injection.
3. EGF neutralising antibody (Polyclonal antibody raised in mouse against human EGF)—Dose 10 µg/injection.
4. Basic FGF neutralising antibody (raised in rabbits against native bovine brain basic FGF)—Dose 30 µg/injection.
5. Acidic FGF neutralising antibody (raised in rabbit against native bovine brain acidic FGF)—Dose 30 µg/injection.

The irrelevant antibodies used for the sham control wounds were either rabbit IgG or goat IgG according to the host in which neutralising antibody to the growth factor was raised. The dose of the irrelevant antibody was similar to that of the neutralising antibody.

SUMMARY OF RESULTS

In all the experiments conducted, no differences were found between the control and sham control wounds at any of the timepoints at which the wounds were examined, thereby indicating an absence of any major effects being produced by the introduction of foreign proteins. Also, no wounds showed impaired healing and the rate of epithelialisation was similar in all treatments.

However, at least in the case of the experimental wounds treated with the neutralising antibodies to TGF-β and PDGF major effects were produced provided treatment was commenced whilst the wounds were still fresh, preferably at or soon after the time of wounding, before or during the granulation phase. Thus, although no major differences were observed between the control wounds and the experimental wounds when treatment was not commenced until the 19th day post-wounding, in other cases, especially when treatment was commenced on the same day as wounding or on the following day, the experimental wounds contained much less collagen I and III compared to the other three wounds in the same animal at any timepoint. There was much greater spacing between the collagen fibrils but their orientation was almost identical to that of normal skin. Indeed, in the neutralising antibody treated wounds, it was often difficult to detect the site of the latter (except for the loss of ectodermal hair follicles). This was in sharp contrast to the other wounds which showed a distinct scar with vertically orientated, parallel, and densely packed collagen fibrils. These effects were most marked in the papillary dermis and subcutaneous tissues. Wounds treated with neutralising antibodies to TGF-β or PDGF also showed a marked reduction in fibronectin, particularly in the reticular dermis, with an orientation pattern similar to that of the collagen fibrils. Although fibronectin staining was markedly reduced throughout the wound, it was still brightest at the dermal/epidermal junction. Treatment with neutralising antibodies to TGF-β and PDGF also decreased the number of blood vessels, monocytes and macrophages within the healing wound. By contrast, the positive control wounds treated with TGF-β and PDGF showed a marked increase in extracellular matrix accumulation, in the density of extracellular matrix packing and in the number of blood vessels, monocytes and macrophages. Scarring was more prominent in these growth factor treated wounds compared to controls.

These results demonstrate the ability of neutralising antibodies to selected growth factors markedly to reduce scar tissue formation in adult dermal wound healing. Most importantly, this advantageous effect was not accompanied by attendant problems of delayed wound healing or delayed epithelialisation and low wound strength.

Some improvement in reducing scar tissue formation was also observed after administering neutralising antibodies to fibroblast growth factors (FGF's) although in the preliminary experimental work it was less marked than in the case of neutralising TGF-β and PDGF growth factors. Interestingly, exogenous acidic or basic FGF itself seemed to improve scarring. It is, however, believed that similar results to TGF-β and PDGF may be achieved, although perhaps to a somewhat lesser extent, with neutralising agents to other growth factors administered at an appropriate dosage level under suitable conditions.

In the case of TGF-3 at least, which appears to be highly active in connection-with the production and organisation of collagen, especially collagen I, leading to the formation of scar tissue, it is believed that normally after the initial injury the level of this growth factor in the environment of the wound may increase quite quickly by means of an autocatalytic cascade effect. Thus, not only does the TGF-β present within an initial wound from platelet degradation act as a chemoattractant to monocytes, macrophages and fibroblasts ay increasing concentrations, but it also feeds back on its own promoter to stimulate its own synthesis so that high levels can soon arise. The inflammatory cells, especially macrophages, release TGF-β and exhibit this auto-inductive effect-on TGF-β synthesis. TGF-β also stimulates the synthesis and release of other growth factors, e.g. TGF-α, PDGF, EGF. TGF-β, and these other growth factors stimulate the synthesis of extracellular matrix molecules, e.g. collagens and glycosaminoglycans, by the wound fibreblasts and also influence the degree of proteolytic turnover and organisation of these extracellular matrix molecules. As the initial fibrin clot is dense, fibreblasts from the adjacent normal skin initially migrate up and down between the clot and the wound margin in a direction broadly perpendicular to the basement membrane. The collagen and other extracellular matrix molecules are also deposited in this abnormal orientation and this eventually gives rise to the scar.

It can be hypothesised that normal wound healing in adults is phylogenetically optimised for speed of closure in adverse healing conditions. Consequently, the quantities of growth factor released are generally excessive, giving the speed of the healing process considerable buffering against external noxious factors but with the long term disadvantage of scarring. Modern methods of wound care, e.g. bandages, and reduction in risks of infection have largely eliminated the necessity of this growth factor "overdrive" so that treatment to diminish the active growth factor profile is permissible and will minimise subsequent scarring.

Thus the autocatalytic cascade of events, described above for TGF-β, is reduced by treatment at an early stage with a neutralising agent. The latter, however, will not be applied in an amount sufficient to neutralize all of this growth factor, thereby leaving sufficient to enable wound healing to proceed without serious inhibition. A similar explanation is also applicable to at least PDGF.

Practical Usage

It will be appreciated that the results obtained from the investigations made in development of this invention have direct practical application in clinical use for controlling scar tissue formation in wound healing, either in therapeutic or cosmetic fields. For practical use, in general an appropriate amount of growth factor antibody or antibodies or other growth factor inhibitory agent(s), constituting the material effective in neutralising and/or in modifying the profile of relevant growth factors active and responsible for scar tissue formation in the healing of wounds, will be made up by any of the methods well-known in the art of pharmacy as a pharmaceutical formulation or preparation for administration in any suitable manner to a patient in need of wound treatment. Such pharmaceutical formulations or preparations may, moreover, be presented not only individually for clinical use but they may also be presented as components of first aid kits for example for non-clinical emergency use.

By way of example in relation to TGF-β and PDGF growth factors, in general the antibody or antibodies or other neutralising agent(s) should be administered (at least for incisional wounds) so as to effectively neutralise between 1 pg–1 µg TGF-β (1 and 2) and/or PDGF (but preferably an amount of between 100 pg–10 ng) per cm linear incision per administration. As previously indicated, application early in the wound healing process is essential. Normally this will be before, during or before and during, the phase of granulation tissue formation, within about 14 days, but preferably within 7 or 3 days, or less, following wounding.

The pharmaceutical preparations may conveniently be applied topically by application to the surface around the wound in liquid, gel, aerosol, cream or powder form, or in the form of a dressing, biodegradeable patch or control release implantable device at the time of wounding or shortly thereafter. Parenteral administration, especially subcutaneous injection, may also often be preferred so that the neutralising antibody or antibodies or other agent(s) can be introduced directly into the wound environment for maximum efficiency. For this purpose the pharmaceutical formulations prepared may comprise sterile liquid preparations (e.g. in phosphate buffered saline) of a predetermined amount of the active material, e.g. relevant antibody or antibodies, presented in unit dosage form and contained in sealed ampoules ready for use. For the alternative topical mode of administration, however, which will be preferred in some cases, the formulations may be made up with the active material in intimate association or admixture with at least one other ingredient constituting a compatible pharmaceutically acceptable carrier, diluent or excipient in order to provide a composition, such as a cream, gel, ointment or the like, which is most suitable for topical application. The formulation may be applied to a sterile dressing, biodegradable, absorbable patches or dressings for topical application, or to slow release implant systems with a high initial release decaying to a slow release.

The formulation may also consist of a neutralising agent, for example, relevent antibody or antibodies, attached to a carrier, for example, a biopolymer of collagen or hyaluronic acid or a polymer, for example, PVC from which it can be released quickly initially and more slowly in the longer term when applied to, or implanted within, the wound or tissue viod.

As will be seen the invention provides a number of different aspects and, in general, it embraces all novel and inventive features and aspects herein disclosed, either explicitly or implicitly and either singly or in combination with one another. Moreover the scope of the invention is not to be construed as being limited by the illustrative examples or by the terms and expressions used herein merely in a descriptive or explanatory sense.

We claim:

1. A method of inhibiting scar tissue formation during the healing of wounds, comprising the steps of administering to a host suffering from tissue wounding a growth factor neutralizing antibody specific against a growth factor selected from the group consisting of TGF-$\beta_1$, TGF-$\beta_2$ and PDGF, wherein the antibody neutralizes the stimulation of macrophage infiltration, fibroblast migration, extracellular matrix synthesis or deposition by fibroblasts, in the wound area before the granulation phase in a dosage effective to reduce activity of the growth factor.

2. A method according to claim 1, wherein the growth factor neutralizing antibody is selected from the group consisting of anti-TGF-$\beta_1$ antibody, anti-TGF-$\beta_2$ antibody, and anti-PDGF-antibody.

3. A method of inhibiting scar tissue formation during the healing of wounds, comprising the steps of administering to a host suffering from tissue wounding a growth factor neutralizing antibody specific against a growth factor selected from the group consisting of TGF-$\beta_1$, TGF-$\beta_2$ and PDGF, wherein the antibody neutralizes the stimulation of macrophage infiltration, fibroblast migration, extracellular matrix synthesis or deposition by fibroblasts, in the wound area during the granulation phase in a dosage effective to reduce activity of the growth factor.

4. A method according to claim 3, wherein the growth factor neutralizing antibody is selected from the group consisting of anti-TGF-$\beta_1$ antibody, anti-TGF-$\beta_2$ antibody, and anti-PDGF-antibody.

5. A method according to claim 1, wherein the growth factor neutralizing antibody is encapsulated.

6. A method according to claim 5, wherein the capsule is degradable by an external stimulus to release the growth factor neutralizing antibody.

7. A method according to claim 6, wherein the external stimulus is selected from the group consisting of UV light, in vivo enzymes, ultrasound and heat.

8. A method according to claim 1, wherein the growth factor neutralizing antibody is bound to a binding molecule.

9. A method according to claim 8, further comprising the step of detaching the binding molecule from the growth factor neutralizing antibody.

10. A method according to claim 9 wherein the binding molecule is detached from the growth factor neutralizing antibody by an external stimulus selected from the group consisting of UV light, in vivo enzymes, ultrasound and heat.

11. A method according to claim 1, further comprising the step of administering the growth factor neutralizing antibody in a pharmaceutically acceptable carrier.

12. A method according to claim 11, wherein the pharmaceutically acceptable carrier is selected from the group consisting of a neutral sterile cream, gel, aerosol and powder for topical application.

13. A method according to claim 11, wherein the pharmaceutically acceptable carrier is selected from the group consisting of a sterile solution for injection, irrigation and inhalation.

14. A method according to claim 11, wherein the pharmaceutically acceptable carrier comprises a sterile dressing for topically covering a wound.

15. A method according to claim 11, wherein the pharmaceutically acceptable carrier is selected from the group consisting of a biopolymer and a polymer for implanting within the wound.

16. A method according to claim 1, further comprising the step of administering a fibroblast growth factor with the growth factor neutralizing antibody.

17. A method according to claim 3, wherein the growth factor neutralizing antibody is encapsulated.

18. A method according to claim 17, wherein the capsule is degradable by an external stimulus to release the growth factor neutralizing antibody.

19. A method according to claim 18, wherein the external stimulus is selected from the group consisting of UV light, in vivo enzymes, ultrasound and heat.

20. A method according to claim 3, wherein the growth factor neutralizing antibody is bound to a binding molecule.

21. A method according to claim 20, further comprising the step of detaching the binding molecule from the growth factor neutralizing antibody.

22. A method according to claim 21 wherein the binding molecule is detached from the growth factor neutralizing antibody by an external stimulus selected from the group consisting of UV light, in vivo enzymes, ultrasound and heat.

23. A method according to claim 3, further comprising the step of administering the growth factor neutralizing antibody in a pharmaceutically acceptable carrier.

24. A method according to claim 23, wherein the pharmaceutically acceptable carrier is selected from the group consisting of a neutral sterile cream, gel, aerosol and powder for topical application.

25. A method according to claim 23, wherein the pharmaceutically acceptable-carrier is selected from the group consisting of a sterile solution for injection, irrigation and inhalation.

26. A method according to claim 23, wherein the pharmaceutically acceptable carrier comprises a sterile dressing for topically covering a wound.

27. A method according to claim 23, wherein the pharmaceutically acceptable carrier is selected from the group consisting of a biopolymer and a polymer for implanting within the wound.

28. A method according to claim 3, further comprising the step of administering a fibroblast growth factor with the growth factor neutralizing antibody.

* * * * *

UNITED STATES PATENT AND TRADEMARK OFFICE
CERTIFICATE OF CORRECTION

PATENT NO. : 5,662,904
DATED : September 2, 1997
INVENTOR(S) : Mark W. J. Ferguson, David M. Foreman and Mamta Shah It is certified that error appears in the above-identified patent and that said Letters Patent is hereby corrected as shown below:

Column 1, Line 5, "no" should be --to--.
Column 2, Line 12, "153" should be --163--.
Column 3, Line 13, "endoral" should be --enteral--.
Column 4, Line 18, "amine" should be --amino--.
Column 4, Line 30, "amine" should be --amino--.
Column 4, Line 52, "and" should be --any--.
Column 6, Line 53, "29" should be --28--.
Column 8, Line 19, "82" should be --µ--.
Column 8, Line 21, after "subjected" insert --to--.
Column 9, Line 56, "TGF-3" should be --TGF-β--.
Column 9, Line 65, "ay" should be --at--.

Signed and Sealed this

Twenty-seventh Day of October, 1998

Attest:

BRUCE LEHMAN

*Attesting Officer*   *Commissioner of Patents and Trademarks*